United States Patent
Winston

(10) Patent No.: US 12,220,405 B2
(45) Date of Patent: Feb. 11, 2025

(54) COMPOSITIONS FOR THE TREATMENT OF HEPATIC STEATOSIS

(71) Applicant: Thomas Winston, Stillwell, KS (US)

(72) Inventor: Thomas Winston, Stillwell, KS (US)

( * ) Notice: Subject to any disclaimer, the term of this patent is extended or adjusted under 35 U.S.C. 154(b) by 522 days.

(21) Appl. No.: 17/342,298

(22) Filed: Jun. 8, 2021

(65) Prior Publication Data
US 2021/0379027 A1 Dec. 9, 2021

Related U.S. Application Data

(60) Provisional application No. 62/705,062, filed on Jun. 9, 2020.

(51) Int. Cl.
| | | |
|---|---|---|
| *A61K 31/436* | (2006.01) | |
| *A61K 31/155* | (2006.01) | |
| *A61K 31/232* | (2006.01) | |
| *A61K 31/353* | (2006.01) | |
| *A61K 38/22* | (2006.01) | |
| *A61K 45/06* | (2006.01) | |
| *A61P 1/16* | (2006.01) | |

(52) U.S. Cl.
CPC .......... *A61K 31/436* (2013.01); *A61K 31/155* (2013.01); *A61K 31/232* (2013.01); *A61K 31/353* (2013.01); *A61K 38/22* (2013.01); *A61K 45/06* (2013.01); *A61P 1/16* (2018.01)

(58) Field of Classification Search
CPC .. A61K 31/436; A61K 31/155; A61K 31/232; A61K 31/353; A61P 1/16
See application file for complete search history.

(56) References Cited

U.S. PATENT DOCUMENTS

2014/0187633 A1* 7/2014 Manku .................. A61K 45/06
514/549

FOREIGN PATENT DOCUMENTS

CN 105147654 A1 12/2015
WO WO-2019118407 A1 * 6/2019 ........... A61K 31/155

OTHER PUBLICATIONS

Koneru et al., "Fisetin protects liver from binge alcohol-induced toxicity by mechanisms including inhibition of matrix metalloproteinases (MMPs) and oxidative stress", Journal of Functional Food, vol. 22, pp. 588-601 (2016).*
Adams et al., "Thyroid Hormone Regulates Hepatic Expression of Fibroblast Growth Factor 21 in a PPARα-dependent Manner", Journal of Biological Chemistry, vol. 285, No. 19, pp. 14078-14082 (2010).*

* cited by examiner

*Primary Examiner* — Kevin E Weddington
(74) *Attorney, Agent, or Firm* — Tracey S. Truitt; Sandberg Phoenix & von Gontard, PC

(57) ABSTRACT

Disclosed herein are pharmaceutical compositions to treat, prevent, reduce the incidence of, or reduce the severity of hepatic steatosis comprising an effective amount of one or more mTOR inhibitors and optionally an effective amount of one or more thyroid hormones. Further disclosed herein are methods of treating, preventing, reducing the incidence of, or reducing the severity of hepatic steatosis comprising administering an effective amount of a pharmaceutical composition of one or more mTOR inhibitors and optionally an effective amount of one or more thyroid hormones.

6 Claims, No Drawings

COMPOSITIONS FOR THE TREATMENT OF HEPATIC STEATOSIS

FIELD

The field of the disclosure relates generally to compositions for the treatment of hepatic steatosis. More specifically, the field of disclosure relates generally to compositions for the treatment of hepatic steatosis that include mammalian target of rapamycin (mTOR) inhibitors and optionally an effective amount of one or more thyroid hormones.

BACKGROUND

Hepatic steatosis (fatty liver) is a condition characterized by a buildup of fat in the liver. Two main types of hepatic steatosis include nonalcoholic fatty liver disease and alcoholic fatty liver disease. Nonalcoholic fatty liver disease is comprised of two forms, simple fatty liver associated with fat accumulation with little or no inflammation or liver cell damage, and nonalcoholic steatohepatitis (NASH) that includes inflammation and liver cell damage associated with fat accumulation. Inflammation and liver cell damage are especially concerning, since these aspects of the disease can cause fibrosis and scarring and can lead to cirrhosis, liver failure and/or liver cancer and may require liver transplantation. Alcoholic fatty liver disease, otherwise known as alcoholic steatohepatitis (ASH), is caused by heavy alcohol use in which the byproducts of the metabolism of alcohol promote inflammation and liver cell damage. ASH is often a precursor to alcoholic hepatitis, which can lead to cirrhosis, liver failure and/or liver cancer and may require liver transplantation.

Hepatic steatosis is a significant problem in the United States and other parts of the world. The prevalence of alcohol-induced hepatic steatosis in the United States is estimated to be about 10% of the population, while the incidence of non-alcoholic hepatic steatosis is estimated to be about 30% of the population. There are currently no pharmacological treatments approved for the treatment of NASH or ASH, and current treatments associated with treating obesity, alcoholism, hyperlipidemia, insulin resistance, and type 2 diabetes have had mixed results. New treatment approaches are needed.

BRIEF DESCRIPTION

Disclosed herein are pharmaceutical compositions to treat, prevent, reduce the incidence of, or reduce the severity of hepatic steatosis comprising an effective amount of one or more mTOR inhibitors and optionally an effective amount of one or more thyroid hormones.

In other aspects, disclosed herein are methods of treating, preventing, reducing the incidence of, or reducing the severity of hepatic steatosis comprising administering an effective amount of a pharmaceutical composition of one or more mTOR inhibitors and optionally an effective amount of one or more thyroid hormones.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or a circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the term "patient" refers to a warm blooded animal such as a mammal which is the subject of a medical treatment for a medical condition that causes at least one symptom. It is understood that at least humans, dogs, cats, and horses are within the scope of the meaning of the term. In some aspects, the patient is human. Generally, as used herein, the term "patient" means a human or an animal for which the compositions of the disclosure may be administered.

As used herein, the terms "treat", "treating", and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms encompass also therapy and cure. Treatment may include any manner in which the symptoms of a pathological condition, disorder, or disease are ameliorated or otherwise beneficially altered.

As used herein, the term "prevent" and "preventing" includes administration of a composition which reduces the frequency of, or delays the onset of, or alleviates the symptoms of a medical condition in a subject relative to a subject which does not receive the composition.

As used herein, the term "reduce the incidence of" refers to a reduction in the number of clinical signs or symptoms of a medical condition in a subject that is administered a composition relative to a subject which does not receive the composition.

As used herein, the term "reduce the severity of" refers to a reduction in the severity of clinical signs or symptoms of a medical condition in a subject that is administered a composition relative to a subject which does not receive the composition.

As used herein, the term "hepatic steatosis" refers to liver disease characterized by excessive fat accumulation in the liver. The term as used herein may encompass nonalcoholic fatty liver disease, nonalcoholic steatohepatitis, alcoholic fatty liver disease, and alcoholic steatohepatitis.

As used herein, the term "mTOR complex 1 (mTORC1)" refers to a protein complex comprising mTOR, regulatory-associated protein of mTOR (RAPTOR), mammalian lethal with SEC13 protein 8 (mLST8), proline-rich AKT substrate of 40 kDa (PRAS40) and DEP domain-containing protein 6 (DEPTOR) that has been described to function as a nutrient/energy/redox sensor; regulator of cellular growth, proliferation, and motility; and controller of protein synthesis with roles in inflammation, autophagy and cell survival.

As used herein, the term "mTOR complex 2 (mTORC2)" refers to a protein complex comprising mTOR, mLST8, DEPTOR, rapamycin-insensitive companion of mTOR (RICTOR), mammalian stress-activated protein kinase interacting protein 1 (mSIN1), and protein observed with rictor 1 and 2 (PROTOR1/2) that has been described to function as an activator of insulin receptors and insulin-like growth hormone factor 1 receptors; and regulator of cell proliferation, cell migration and cytoskeletal remodeling with roles in signaling the production of cytokines, inflammation and cell survival.

As used herein, the term "mTOR inhibitor (mTOR Inhibitor)" refers to a composition that either directly or indirectly inhibits one or more functions of mTOR, mTORC1, mTORC2 and combinations thereof. Examples of suitable mTOR inhibitors include omega-3 fatty acid derivatives, biguanide antihyperglycemic agents, flavonoids, macrolides, and other agents that effectively inhibit one or more mTOR protein complex functions.

As used herein, the term "thyroid hormone" refers to a composition that is either equivalent to, a derivative of, or affects the same functions as triiodothyronine (T3). Examples of suitable thyroid hormones include liothyronine, a T3 thyroid hormone composition.

Without being bound by theory, it is believed that the pathology of hepatic steatosis is similar in many respects whether it is associated with the use of heavy volumes of alcohol, as in ASH, or not, as in NASH. Hepatic steatosis is characterized by an accumulation of lipid droplets in the cytoplasm of the hepatocytes. The disease is generally diagnosed when greater than 50% of hepatocytes are involved in accumulation of lipids. The excess accumulation of lipids can lead to fat cysts that form and may subsequently rupture. The presence and growth of the fat cysts and/or their rupturing can trigger inflammation and other immune responses. Damage to the hepatocytes can involve certain changes to the structure and function of the cellular membranes and cytoskeleton that cause the cells to undergo transformation, leading to fibrosis, cirrhosis, necrosis, apoptosis and/or hepatocarcinoma.

It is also believed that a diet that is rich in omega-6 fatty acids compared to omega-3 fatty acids can predispose individuals to hepatic steatosis as a result of an increase in the production of pro-inflammatory arachidonic acid-derived eicosanoids. Also, some of the cellular changes believed to occur in hepatic steatosis associated with an increase in omega-6 to omega-3 fatty acids in the cellular membranes may interfere with the normal presentation and function of certain membrane-bound receptors including cell bound enzymes, calcium channels, sodium channels, potassium channels, other ion channels and other signaling proteins. As a result, the membrane bound proteins may become less responsive to stimuli including hormones, cell signaling proteins and cell signaling substances, which may in part be due to oxidative stress over time leading to changes in mTOR complex gene regulation and degradation of the omega-3 to omega-6 fatty acid ratio in cellular membranes. It is believed that omega-3 fatty acids may increase cell membrane fluidity in the body of a patient to improve cell membrane and membrane protein functions. Omega-3 fatty acids may also enhance mitochondrial membrane function and enhance the production of Acetyl-CoA, which is a substrate in both the citric acid cycle and fatty acid β-oxidative metabolism. Thus, the effects of omega-3 fatty acids may improve energy production in the cell overall. Without being bound by theory, is it also believed that inflammation and improper immune response are contributing factors for the development of hepatic steatosis. It is believed that an inflammatory environment exists that is promoted by inflammatory cytokines and other chemicals, some of which are released from cell membranes as a result of an imbalance of the ratio of omega-3 to omega-6 fatty acids and some of which are released from senescent cells that accumulate over time during the aging process.

Without being bound by theory, it is also believed that mTORC1 and mTORC2 control multiple diffuse aspects of cellular metabolism, cellular integrity, cellular death, immune response and inflammation. It is believed that the mTORC1 and mTORC2 activity is enhanced and driven upwards by cytokine release including those released as a result of higher than optimal ratios of omega-6 to omega-3 fatty acids in the cell membrane and that mTORC1 and mTORC2 complex functions may be down regulated by the use of mTOR inhibitors. Examples of suitable mTOR inhibitors may include omega-3 fatty acid derivatives, biguanide antihyperglycemic agents, flavonoids, macrolides, and other agents that effectively inhibit mTOR protein complexes.

It is further believed that part of the maintenance of the cell membrane may involve maintaining an optimal ratio of omega-3 to omega-6 fatty acids, which results in an anti-inflammatory effect. It is believed that increasing the ratio of omega-3 to omega-6 fatty acids will lead to a decrease or an inhibition of cytokine production and a reduction of the signaling and release of inflammatory mediators.

Examples of omega-3 fatty acids include eicosapentaenoic acid (EPA) and docosahexaenoic acid (DHA), which are generally derived from diet. It is believed that EPA is superior to DHA for inhibition of inflammation and maintaining cell integrity. It is believed that omega-6 fatty acids (e.g. arachidonic acids) are precursors to the formation of cytokines. It is believed that omega-3 fatty acids may help to decrease cytokine production, for example, from the action of eicosanoid molecules. Accordingly, a decrease of omega-3 fatty acids, in relation to omega-6, may facilitate an inflammatory response caused by cytokines.

Without being bound by theory, it is believed that therapies including omega-3 fatty acids may downshift cellular signaling by decreasing cytokine formation. This may increase the maintenance of cellular adhesion and normal membrane anatomy with better sodium, potassium and calcium channel function and better response to stimuli from hormones, cell signaling proteins and other cell signaling substances such as nitric oxide. Therapies including omega-3 fatty acids may also facilitate the maintenance of membranes of mitochondria and other intracellular structures.

It is further believed that control over mTOR-associated protein complexes may also be of importance in the treatment, prevention, reduction in the incidence of and reduction in the severity of hepatic steatosis. It is believed that mTOR-associated protein complexes may respond to stimuli that alter cellular metabolism and growth. The mTOR-associated protein complexes may be involved in many diseases and almost all tissues of the body, including hepatic steatosis and hepatic carcinoma. It is believed that the dysregulation of mTORC1 and mTORC2 may be an underlying cause of disease over one's lifetime. It is also believed that overactivity of these protein complexes may lead to a higher incidence and severity of hepatic steatosis and hepatic carcinoma. It is further believed that treatments that include mTOR inhibitors may enhance the treatment, prevention, reduction of the incidence of, or reduction of the severity of hepatic steatosis.

Without being bound by theory, it is believed that mTOR-associated protein complexes are critical in the regulation of metabolism and inflammation in key metabolic tissues including hepatic tissue. It is further believed that hepatic steatosis is strongly associated with insulin resistance and glucose intolerance that can result from the dysregulated activation of mTOR-associated protein complex activity. It is also believed that biguanide antihyperglycemic agents act through inhibition of the mTORC2 complex to modulate cell functions including metabolism, proliferation, migration and survival as well as reduce oxidative stress and inflammation. It is further believed that biguanide antihyperglycemic agents inhibit the mTORC2 complex by mechanisms including the reduction of the downstream effects of the AKT protein that is a component of the PI3K/AKT/mTOR pathway. By reducing the downstream metabolic effects, oxidative stress and inflammation associated with the PI3K/AKT/mTOR pathway, biguanide antihyperglycemic agents may be effective in treating, preventing, reducing the incidence of or reducing the severity of hepatic steatosis.

Without being bound by theory, it is believed that certain flavonoids act as senolytic agents by reducing mTOR complex activity, increasing the activity of sirtuins, and increasing the activity of AMP-activated protein kinase (AMPK). These actions are believed to play a role in cellular energy homeostasis and promotion of apoptosis in senescent cells that are resistant to signaling proteins and accumulate during the aging process. It is further believed that the accumulation of senescent cells results from a weakened immune system related to aging, and these cells provide a source of chronic inflammation through the release of inflammatory chemicals and may lead to an increased risk of hepatic steatosis and hepatic carcinoma. It is also believed that the mechanistic actions of certain flavonoids used in combination with a biguanide antihyperglycemic agent can exhibit synergistic effects for promoting apoptosis in senescent cells while promoting homeostasis in normal cells. It is further believed that when certain flavonoids are combined with certain galactomannans, the absorption of the certain flavonoids can be increased by as much as 25-fold.

Certain flavonoids, including fisetin, acting at least as a senolytic, is believed to enhance the activity of icosapent ethyl by causing cellular break down. Fisetin is also believed to affect the PI3K/AKT/mTOR pathway by downregulating the signaling pathway and enhancing lipid metabolism through its senolytic activity leading to cellular death. Fisetin is also believed to decrease inflammatory chemical production and/or release in the body, which is expected to decrease the risk of many other diseases associated with or exacerbated by inflammation.

Without being bound by theory, it is believed that combining mTOR inhibitors may facilitate the treatment, prevention, reduction of the incidence of, or reduction of the severity of hepatic steatosis. It is also believed that a composition comprised of one or more mTOR inhibitors may be more effective if the composition is comprised of at least two or more mTOR inhibitors.

Thyroid hormones, including e.g. liothyronine (a T3 thyroid hormone), are believed to assist in controlling metabolism by utilizing oxygen and calories for conversion into energy in the mitochondria through the formation of ATP. Thyroid hormones are believed to be necessary for energy production in all organs, especially in muscle, brain, heart, and other tissues. Increased levels of thyroid hormones are believed to affect increased levels of cellular metabolism. Various tests are available to determine thyroid hormone levels, e.g. by measuring the amount of thyroid hormone levels in the blood. Thyroid hormones are believed to enhance cell survival and the metabolism of fats, proteins and carbohydrates. It is further believed that treatment comprising one or more thyroid hormones in combination with a flavonoid, such as fisetin may act synergistically to increase fat metabolism and promote the senolytic effects of fisetin.

Thyroid hormones are believed to affect nearly every cell of the body through receptors in the nucleus of the cell. Thyroid hormones bind to DNA-binding nuclear hormone receptors, cause conformational changes in the receptors, and activate transcription of the thyroid hormone sensitive genes by either initiating expression or upregulation. Also, functions of the PI3K/AKT pathway are believed to include regulation of cell adhesion, cell cycle progression, cell survival and signaling. Precursors to the thyroid hormones, referred to as T4 or thyroxine, are believed to stimulate the PI3/AKT pathway in the cytoplasm, whereas T3 does not. T3 also has a shorter half-life than T4, so T3 is recommended for the treatment of hepatic steatosis over T4.

Without being bound by theory, it is believed that rapamycin is primarily an mTOR1 inhibitor at lower doses and for short treatment cycles, whereas high levels and very prolonged treatment cycles can also inhibit mTOR2 by blocking mTOR2 production by the cell. Rapamycin treatment is normally administered continuously either orally or intravenously, which frequently causes side effects of insulin resistance and hyperglycemia, and causes immune deficiency. Also, long-term treatment with rapamycin may decrease antigen processing and inhibit T-cell proliferation leading to suppression of the immune system. Rapamycin is also believed to decrease the phosphorylation of the ribosomal s6 kinase, S6K1, which is believed to result in active decreases in protein synthesis and cell mortality.

It is believed that treatment regimens that included rapamycin could be effective and safe if rapamycin is dosed at low-levels either intermittently or in conjunction with other mTOR inhibitors and/or additional medications that decrease or down regulate the PI3K-AKT pathway. It is further believed that using a biguanide antihyperglycemic agent, such as metformin, in these treatment regimens will allow for down regulation of both mTOR1 and mTOR2 safely without causing significant side effects of high-dose rapamycin. In addition to acting as an inhibitor of mTOR2, metformin also decreases glycolysis and is effective in controlling blood glucose levels. The addition of a flavonoid, such as fisetin, is believed to provide the added benefit of promoting apoptosis or cell death of senolytic cells effectuated at least partly through its inhibition of the mTOR pathway. The effects of fisetin may be further improved with the addition of a T3 thyroid hormone. It is believed that synergy of activity for inhibition of the PI3K-AKT pathway can be achieved with the combination of rapamycin, metformin, and fisetin while providing a low risk of side effects. The treatment regimens could further benefit from the addition of an omega-3 fatty acid derivative, which is believed to downregulate mTOR2, decrease cytokine formation, strengthen cell membranes and structures, and decrease phosphorylation of phosphatides. Additionally, the addition of a T3 thyroid hormone is believed to enhance the effectiveness of the therapy regimen. These combination therapies are believed to have minimal side effects, may be administered continuously over long periods of time, and result in an effective decrease in PI3K-AKT activity. Without being bound by theory, it is believed that the synthesis of nicotinamide adenine dinucleotide (NAD+), which is at least synthesized from vitamin B3, is decreased as we age and possibly as a result of obesity. NAD+ is believed to have several functions including its role in mitochondrial function and energy production, and as a coenzyme in both β-oxidation and glucose metabolism, including the formation of lactate from pyruvate. It is also believed that metformin inhibits gluconeogenesis and promotes the reduction of body fat by acceleration of the β-oxidative pathway. Omega-3 fatty acids, like icosapent ethyl, is believed to facilitate this metabolic pathway by enhancing the transport and metabolism of fats. It is also believed that NAD+ and adenosine diphosphate ribose have a role in controlling the activity of enzymes involved in cellular homeostasis and DNA repair, including sirtuins and polymerases. Thus, it is believed that administration of NAD+ may help reduce the increased cancer rate that is observed in overweight and obese individuals.

In various embodiments, the compositions of the disclosure include compositions for the treatment of hepatic steatosis. In various embodiments, the compositions of the disclosure include an effective amount of one or more mTOR inhibitors and optionally an effective amount of one or more thyroid hormones. In various embodiments, suitable mTOR inhibitors may include omega-3 fatty acid derivatives, biguanide antihyperglycemic agents, flavonoids, macrolides, and other agents that effectively inhibit mTOR protein complexes. In various embodiments, suitable thyroid hormones may include a T3 hormone, such as liothyronine. In various embodiments, the compositions of the disclosure may further include effective amounts of one or more other active agents, such as vitamin B derivatives, quercetin, resveratrol, and NAD+.

Preferentially, at least one of the components of the composition will decrease inflammation associated with hepatic steatosis.

Preferentially, at least one of the components of the composition will decrease the rate of normal cell death or will increase the life span of normal cells including hepatocytes and cells involved in immune response systems.

Preferentially, at least one of the components of the composition will enhance hepatocellular membrane integrity and function and/or induce apoptosis in senescent cells. Preferentially, the compositions of the disclosure include a flavonoid, such as fisetin, at doses that are high enough to cause senescent cells to die and results in an overall decrease in inflammation in the patient.

Preferentially, the compositions of the disclosure include at least an effective amount of a biguanide antihyperglycemic agent in combination with an effective amount of an omega-3 fatty acid derivative.

Preferentially, other than promoting euthyroid in patients, the compositions of the disclosure include a thyroid hormone concurrent with high doses of a flavonoid, such as fisetin.

In various embodiments, the compositions may include an effective amount of an omega-3 fatty acid derivative. Suitable omega-3 fatty acid derivatives may include icosapent ethyl. In various embodiments, the compositions of the disclosure may include an effective amount of at least about 0.5 g of icosapent ethyl, or between about 0.5 g to about 10.0 g, or 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 g, or any range between any two of these amounts including about 0.5 g to about 10.0 g, or about 1.0 g to about 7.0 g, or about 2.0 g to about 8.0 g. In some preferred forms, the amount of icosapent ethyl is sufficient to maintain an optimum level of icosapent ethyl in the blood of a subject receiving an administration of the composition on a daily basis.

In various embodiments, the compositions of the disclosure may include an effective amount of icosapent ethyl that will result in an increase in EPA of at least about 10% to about 400% or more, or 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400% or more over the course of a year when compared to the starting EPA value for a patient prior to receiving the composition.

In various embodiments, the compositions of the disclosure may include an effective amount of icosapent ethyl that will result in a decrease in the ratio of arachidonic acid to EPA by at least about 10% to about 200% or more, or 10, 20, 30, 40, 50, 60, 70, 80, 90, 100, 110, 120, 130, 140, 150, 160, 170, 180, 190, 200% or more over the course of a year when compared to the starting ratio of arachidonic acid to EPA for a patient prior to receiving the composition.

In various embodiments, the compositions of the disclosure may include an effective amount of icosapent ethyl that will result in an increase in the level of red blood cells by at least about 25% to about 1000% or more, or 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000% or more over the course of a year when compared to the starting level of red blood cells for a patient prior to receiving the composition.

In various embodiments, the compositions of the disclosure may include an effective amount of a biguanide antihyperglycemic agent. Suitable biguanide antihyperglycemic agents include metformin. In various embodiments, the compositions may include an effective amount of at least about 50 mg of biguanide antihyperglycemic agent, or between about 50 mg to about 4000 mg, or 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2025, 2050, 2075, 2100, 2125, 2150, 2175, 2200, 2225, 2250, 2275, 2300, 2325, 2350, 2375, 2400, 2425, 2450, 2475, 2500, 2525, 2550, 2575, 2600, 2625, 2650, 2675, 2700, 2725, 2750, 2775, 2800, 2825, 2850, 2875, 2900, 2925, 2950, 2975, 3000, 3025, 3050, 3075, 3100, 3125, 3150, 3175, 3200, 3225, 3250, 3275, 3300, 3325, 3350, 3375, 3400, 3425, 3450, 3475, 3500, 3525, 3550, 3575, 3600, 3625, 3650, 3675, 3700, 3725, 3750, 3775, 3800, 3825, 3850, 3875, 3900, 3925, 3950, 3975, or 4000 mg or any range between any two of these amounts including about 250 mg to about 4000 mg, about 250 mg to about 3000 mg, about 250 mg to about 500 mg, about 250 mg to about 750 mg, 250 mg to about 1000 mg, about 250 mg to about 1250 mg, about 250 mg to about 1500 mg, or between about 500 mg to about 3000 mg.

In various embodiments, the compositions may include an effective amount of a flavonoid. Suitable flavonoid agents include fisetin and fisetin derivatives. In various embodiments, the compositions may include an effective amount of at least about 10 mg/kg of patient body weight of a flavonoid, or between about 10 mg/kg to about 100 mg/kg of patient body weight, or 10, 15, 20, 25, 30, 35, 40, 45, 50, 55, 60, 65, 70, 75, 80, 85, 90, 95, or 100 mg/kg of patient body weight or any range between any two of these amounts including about 10 mg/kg to about 20 mg/kg, about 15 mg/kg to about 25 mg/kg, about 20 mg/kg to about 30 mg/kg, about 25 mg/kg to about 50 mg/kg, or about 20 mg/kg to about 100 mg/kg of a flavonoid. In some preferred forms, the amount of fisetin is sufficient to maintain an optimum level of fisetin in the blood of a subject receiving an administration of the composition, such optimum level may be achieved by combining the fisetin with a galactomannan to enhance the absorption of the flavonoid.

In various embodiments, the compositions may include an effective amount of a flavonoid. Suitable flavonoid agents include fisetin and fisetin derivatives. In various embodiments, the compositions may include an effective amount of at least about 50 mg of a flavonoid, or between about 50 mg to about 750 mg, or 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750 mg or any range between any two of these amounts including about 50 mg to about 500 mg, about 100 mg to about 750 mg, about 250 mg to about 500 mg, about 250 mg to about 750 mg, about 500 mg to about 750 mg, or about 100 mg to about 500 mg of a flavonoid. In some preferred forms, the amount of fisetin is sufficient to maintain an optimum level of fisetin in the blood of a subject receiving an administration of the composition; such optimum level may be achieved by combining the fisetin with a galactomannan to enhance the absorption of the flavonoid.

In various embodiments, the compositions may include an effective amount of a macrolide. Suitable macrolides include rapamycin. In various embodiments, the compositions may include an effective amount of a macrolide of at least about 0.1 mg of a macrolide, or between about 0.1 mg to about 10 mg, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mg or any range between any two of these amounts including about 2.0 mg to about 6.0 mg, about 1.0 mg to about 10.0 mg, about 2.0 mg to about 4.0 mg, about 2.5 mg to about 5.0 mg, about 2.5 mg to about 7.5 mg, or about 1.0 mg to about 5.0 mg of a macrolide. In some preferred forms, the amount of rapamycin is administered as a loading dose followed by a lower daily dose. In some preferred forms, the amount of rapamycin is sufficient to maintain an optimum level of rapamycin in the blood of a subject receiving an administration of the composition; such optimum level may be determined as a preferred optimum trough level as measured in nanograms per ml of blood. In some preferred forms, the administration of rapamycin is provided intermittently at low levels.

In various embodiments, the compositions may include an effective amount of a thyroid hormone. Suitable thyroid hormones include the T3 liothyronine. In various embodiments, the compositions of the disclosure may include an effective amount of at least about 1 μg of liothyronine, or between about 1 μg to about 250 μg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 μg, or any range between any two of these amounts including about 5 μg to about 150 μg, or about 10 μg to about 100 μg, or about 10 μg to about 25 μg, or about 25 μg to about 150 μg, or about 25 μg to about 250 μg. In some preferred forms, the amount of liothyronine is sufficient to maintain an optimum level of liothyronine in the blood of a subject receiving an administration of the composition.

In various embodiments, the compositions may further include an effective amount of a vitamin B derivative. Suitable vitamin B derivatives include nicotinamide riboside. In various embodiments, the compositions include an effective amount of at least about 50 mg of nicotinamide riboside, or about 50 mg to about 1000 mg of nicotinamide riboside, including about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 mg, or any range between any two of these amounts, or about 100 mg to about 750 mg, or about 200 mg to about 500 mg of nicotinamide riboside.

In various embodiments, the compositions further include an effective amount of quercetin. In various embodiments, the compositions may include an effective amount of at least about 100 mg to about 1000 mg, including about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of quercetin.

In various embodiments, the compositions may further include an effective amount of resveratrol. In various embodiments, the compositions may include an effective amount of at least about 100 mg to about 1000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of resveratrol.

In various embodiments, the compositions may further include an effective amount of NAD+. In various embodiments, the compositions may include an effective amount of at least about 100 mg to about 2000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 mg, or any range between any two of these amounts, or about 300 mg to about 1200 mg, or about 300 mg to about 600 mg of NAD+. In various embodiments, the compositions including NAD+ may be further supplemented with adenosine diphosphate ribose.

In various embodiments, the compositions may include an effective amount of a combination of one or more mTOR inhibitors with an effective amount of one or more thyroid hormones. In various embodiments, the compositions may include an effective amount of one or more mTOR inhibitors with an effective amount of one or more thyroid hormones and an effective amount of a flavonoid. In various embodiments, the compositions may include an effective amount of one or more mTOR inhibitors with an effective amount of one or more thyroid hormones and an effective amount of a high dose of a flavonoid, which is associated with a senolytic effect.

In various embodiments, the compositions of the disclosure may further contain additional pharmaceutically acceptable carriers. The pharmaceutical compositions may, for example, be in a form suitable for oral administration as a tablet, capsule, pill, powder, sustained release formulation, solution or suspension, in a form suitable for parenteral injection as a sterile solution, suspension, or in a form of an emulsion for topical administration as an ointment or cream or for rectal administration as a suppository. The pharmaceutical compositions may be in unit dosage forms suitable for single administration of precise dosages. The pharmaceutical compositions may include conventional pharmaceutical carriers or excipients. In addition, the compositions may include other medicinal or pharmaceutical agents, carriers, adjuvants, etc.

In various embodiments, the compositions may be administered to a patient through any suitable route of administration effective in delivering an amount of active agent or active agents to a patient. Suitable routes of administration include oral, parenteral, enteral, and rectal or the like.

In some forms, the composition will comprise each of the ingredients in a single administration form, such as a pill, tablet, capsule, oral solution, injection solution, infusion solution, or any of the forms described herein. In other forms, the composition will comprise a kit comprising each of the individual ingredients, together with instructions for administering each ingredient. In some forms of the kit, certain ingredients will already be combined such that two, three, or more of the components or ingredients of the composition are in a single administration form as described herein.

Various embodiments of the disclosure further relate to methods of treating hepatic steatosis that include administering a composition of an effective amount of one or more mTOR inhibitors and optionally an effective amount of one or more thyroid hormones. In various embodiments, suitable mTOR inhibitors may include omega-3 fatty acid derivatives, biguanide antihyperglycemic agents, flavonoids, macrolides, and other agents that effectively inhibit mTOR protein complexes.

In various embodiments, suitable thyroid hormones may include a T3 hormone, such as liothyronine. In various embodiments, the methods of treating hepatic steatosis include administering compositions that further include effective amounts of one or more other active agents, such as vitamin B derivatives, quercetin, resveratrol, and NAD+.

In various embodiments, the methods may include administering an effective amount of an omega-3 fatty acid derivative. Suitable omega-3 fatty acid derivatives may include icosapent ethyl. In various embodiments, the methods may include administering an effective amount of at least about 0.5 g of icosapent ethyl, or between about 0.5 g to about 10.0 g, or 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 g, or any range between any two of these amounts including about 0.5 g to about 10.0 g, or about 1.0 g to about 7.0 g, or about 2.0 g to about 8.0 g once, twice, or three or more times daily. In some preferred forms, the amount of icosapent ethyl is sufficient to maintain an optimum level of icosapent ethyl in the blood of a subject receiving an administration of the composition.

In various embodiments, the method may include administering an effective amount of a biguanide antihyperglycemic agent. Suitable biguanide antihyperglycemic agents include metformin. In various embodiments, the methods may include administering an effective amount of at least about 50 mg of biguanide antihyperglycemic agent, or between about 50 mg to about 4000 mg, or 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2025, 2050, 2075, 2100, 2125, 2150, 2175, 2200, 2225, 2250, 2275, 2300, 2325, 2350, 2375, 2400, 2425, 2450, 2475, 2500, 2525, 2550, 2575, 2600, 2625, 2650, 2675, 2700, 2725, 2750, 2775, 2800, 2825, 2850, 2875, 2900, 2925, 2950, 2975, 3000, 3025, 3050, 3075, 3100, 3125, 3150, 3175, 3200, 3225, 3250, 3275, 3300, 3325, 3350, 3375, 3400, 3425, 3450, 3475, 3500, 3525, 3550, 3575, 3600, 3625, 3650, 3675, 3700, 3725, 3750, 3775, 3800, 3825, 3850, 3875, 3900, 3925, 3950, 3975, or 4000 mg or any range between any two of these amounts including about 250 mg to about 4000 mg, about 250 mg to about 3000 mg, about 250 mg to about 500 mg, about 250 mg to about 750 mg, 250 mg to about 1000 mg, about 250 mg to about 1250 mg, about 250 mg to about 1500 mg, or between about 500 mg to about 3000 mg once, twice, or three or more times daily.

In various embodiments, the methods may include administering an effective amount of a flavonoid. Suitable flavonoid agents include fisetin and fisetin derivatives. In various embodiments, the methods may include administering an effective amount of at least about 10 mg/kg of patient body weight of a flavonoid, or between about 10 mg/kg to about 100 mg/kg of patient body weight, or 10, 15, 20, 25, 30, 35, 40, 45, 50, 55, 60, 65, 70, 75, 80, 85, 90, 95, or 100 mg/kg of patient body weight or any range between any two of these amounts including about 10 mg/kg to about 20 mg/kg, about 15 mg/kg to about 25 mg/kg, about 20 mg/kg to about 30 mg/kg, about 25 mg/kg to about 50 mg/kg, or about 20 mg/kg to about 100 mg/kg once, twice, or three or more times daily, weekly, monthly, trimonthly or intermittently with periods between administration when no flavonoid is administered. In some preferred methods, the flavonoid may be administered only one or two days per week, or only one or two days every two weeks, or only one or two days every three weeks or only one or two days per month, bimonthly or trimonthly. In some preferred methods, the flavonoid may be administered each day at the highest specified dose that the patient can tolerate. In various embodiments, the flavonoid or high dose of the flavonoid may include long-term administration, possibly for the life of the patient. In some preferred methods, the amount of fisetin is sufficient to maintain an optimum level of fisetin in the blood of a subject receiving an administration of the composition; such optimum level may be achieved by combining the fisetin with a galactomannan to enhance the absorption of the flavonoid. In various embodiments, a higher dose of fisetin may be associated with a senolytic effect. In various embodiments, a lower dose of fisetin may be associated with an antioxidant effect.

In various embodiments, the methods may include administering an effective amount of a flavonoid that is administered on a daily basis. Suitable flavonoid agents include fisetin and fisetin derivatives. In various embodiments, the methods may include administering an effective amount of a flavonoid of at least about 50 mg of a flavonoid, or between about 50 mg to about 750 mg, or 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750 mg or any range between any two of these amounts including about 50 mg to about 500 mg, about 100 mg to about 750 mg, about 250 mg to about 500 mg, about 250 mg to about 750 mg, about 500 mg to about 750 mg, or about 100 mg to about 500 mg once, twice, or three or more times daily. In some preferred methods, the flavonoid may be administered only one or two days per week, or only one or two days every two weeks, or only one or two days every three weeks or only one or two days per month, bimonthly or trimonthly. In some preferred methods, the flavonoid may be administered each day at the highest specified dose that the patient can tolerate. In various embodiments, the flavonoid or high dose of the flavonoid may include long-term administration, possibly for the life of the patient. In some preferred methods, the amount of fisetin is sufficient to maintain an optimum level of fisetin in the blood of a subject receiving an administration of the composition; such optimum level may be achieved by combining the fisetin with a galactomannan to enhance the absorption of the flavonoid. In various embodiments, a higher dose of fisetin may be associated with a senolytic effect. In various embodiments, a lower dose of fisetin may be associated with an antioxidant effect.

In various embodiments, the methods may include administering an effective amount of a macrolide. Suitable macrolides include rapamycin. In various embodiments, the methods may include administering an effective amount of a macrolide of at least about 0.1 mg of a macrolide, or between about 0.1 mg to about 10 mg, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mg or any range between any two of these amounts including about 2.0 mg to about 6.0 mg, about 1.0 mg to about 10.0 mg, about 2.0 mg to about 4.0 mg, about 2.5 mg to about 5.0 mg, about 2.5 mg to about 7.5 mg, or about 1.0 mg to about 5.0 mg of a macrolide. In some preferred forms, the amount of rapamycin is administered as a loading dose followed by a lower daily dose. In some preferred forms, the amount of rapamycin is sufficient to maintain an optimum level of rapamycin in the blood of a subject receiving an administration of the composition; such optimum level may be determined as a preferred optimum trough level as measured in nanograms per ml of blood. In some preferred forms, the administration of rapamycin is provided intermittently at low levels.

In various embodiments, the methods may include administering an effective amount of an omega-3 fatty acid derivative in a dosing regimen with an effective amount of a biguanide antihyperglycemic agent.

In various embodiments, the methods may include administering an effective amount of an omega-3 fatty acid derivative in a dosing regimen with an effective amount of a flavonoid.

In various embodiments, the methods may include administering an effective amount of an omega-3 fatty acid derivative in a dosing regimen with an effective amount of a biguanide antihyperglycemic agent and an effective amount of a flavonoid.

In various embodiments, the methods may include administering an effective amount of a biguanide antihyperglycemic agent in a dosing regimen with an effective amount of a flavonoid.

In various embodiments, the methods may include administering an effective amount of a thyroid hormone. Suitable thyroid hormones include the T3 liothyronine. In various embodiments, the methods of the disclosure may include administering an effective amount of at least about 1 µg of liothyronine, or between about 1 µg to about 250 µg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 µg, or any range between any two of these amounts including about 5 µg to about 150 µg, or about 10 µg to about 100 µg, or about 10 µg to about 25 µg, or about 25 µg to about 150 µg, or about 25 µg to about 250 µg either weekly, bimonthly, or monthly; however, thyroid hormones should not be given daily and administration should not exceed three days per week. In some preferred methods, the administration of thyroid hormones is dependent upon the clinical response and tolerance of the patient and may continue long-term including many years. In some preferred methods, the amount of liothyronine administered is sufficient to maintain an optimum level of liothyronine in the blood of a subject receiving an administration of the composition.

In various embodiments, the methods may include diagnosing thyroid functions in each patient prior to administration of an effective amount of a thyroid hormone. In various embodiments, the methods for patients requiring thyroid hormone replacement in order to establish normal thyroid functions may preferentially be administered a T3 thyroid hormone. In various embodiments, patients with normal thyroid functions may be administered a low dose of a T3 thyroid hormone (e.g. 5 to 10 µg of liothyronine) combined with a high dose of a flavonoid. In various embodiments, the methods may include administering a combination of a low dose of a T3 thyroid hormone and a high dose of a flavonoid that effectively elicits a synergistic effect of increasing fat metabolism and promoting cellular senescence. In various embodiments, other than promoting euthyroid in patients, the methods include administering a thyroid hormone concurrent with high doses of a flavonoid, such as fisetin.

In various embodiments, the methods may include administering an effective amount of a vitamin B derivative. Suitable vitamin B derivatives include nicotinamide riboside. In various embodiments, the methods may include administering an effective amount of at least about 50 mg of nicotinamide riboside, or about 50 mg to about 1000 mg of nicotinamide riboside, including about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 mg, or any range between any two of these amounts, or about 100 mg to about 750 mg, or about 200 mg to about 500 mg nicotinamide riboside once, twice, or three or more times daily.

In various embodiments, the methods may include administering an effective amount of quercetin. In various embodiments, the methods may include administering an effective amount of at least about 100 mg to about 1000 mg, including about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of quercetin once, twice, or three or more times daily.

In various embodiments, the methods may include administering an effective amount of resveratrol. In various embodiments, the methods may include administering an effective amount of at least about 100 mg to about 1000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of resveratrol once, twice, or three or more times daily.

In various embodiments, the methods may include administering an effective amount of NAD+. In various embodiments, the methods may include administering an effective amount of at least about 100 mg to about 2000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 mg, or any range between any two of these amounts, or about 300 mg to about 1200 mg, or about 300 mg to about 600 mg of NAD+ once, twice, or three or more times daily. In various embodiments, the methods that include administering NAD+ may be further supplemented with adenosine diphosphate ribose. In various embodiments, the methods may include administering NAD+ at a lower daily dose when it is administered in combination with a high dose of fisetin and T3, such lower dose of NAD+ being about half of the dose administered otherwise.

In various embodiments, the methods may include administering an effective amount of a combination of thyroid hormones. Suitable thyroid hormones that may be included in the combination include the T3 liothyronine. In various embodiments, the methods may include administering an effective amount of a combination of one or more thyroid hormones with an effective amount of a flavonoid. In various embodiments, the methods may include administering an effective amount of one or more thyroid hormones and an effective amount of a high dose of a flavonoid, which is associated with a senolytic effect unless the patient is hypo thyroid on the days of the week the thyroid hormone is administered. In various embodiments, the methods may include administering a combination of an effective amount of one or more thyroid hormones with either an effective amount of a flavonoid or a high dose of a flavonoid, wherein only some of the compositions that include an effective amount of a flavonoid also include an effective amount of one or more thyroid hormones. For example, an effective amount of one or more thyroid hormones may be included only in one of two weekly compositions administered that includes an effective amount of a flavonoid or a high dose of a flavonoid, which composition could be either the first or second weekly composition administered that includes a flavonoid or high dose flavonoid.

In various embodiments, the methods may include administering an effective amount of a combination of one or more mTOR inhibitors with an effective amount of one or more thyroid hormones. In various embodiments, the methods may include administering an effective amount of one or more mTOR inhibitors with an effective amount of one or more thyroid hormones and an effective amount of a flavonoid. In various embodiments, the methods may include administering an effective amount of one or more mTOR inhibitors with an effective amount of one or more thyroid hormones and an effective amount of a high dose of a flavonoid, which is associated with a senolytic effect. In various embodiments, the methods may include administering a combination of an effective amount of one or more mTOR inhibitors with an effective amount of one or more thyroid hormones and either an effective amount of a flavonoid or a high dose of a flavonoid, wherein only some of the compositions that include an effective amount of a flavonoid also include an effective amount of one or more thyroid hormones. For example, an effective amount of one or more thyroid hormones may be included only in one of two weekly compositions administered that includes an effective amount of a flavonoid or a high dose of a flavonoid, which composition could be either the first or second weekly composition administered that includes a flavonoid or high dose flavonoid. In various embodiments, the one or more thyroid hormones should be administered for short durations (for example, two days a week, bimonthly, or monthly) during any periods of a dosing regimen that include a high dose of a flavonoid.

In some preferred forms, the methods include administering a macrolide, such as rapamycin; in combination with a biguanide antihyperglycemic agent, such as metformin; in combination with an omega-3 fatty acid derivative, such as icosapent ethyl; in combination with a flavonoid, such as fisetin; and in combination with a T3 thyroid hormone, such as liothyronine. In some preferred forms, the methods include administering a macrolide, such as rapamycin, dosed weekly to achieve blood levels below specified levels measured at specified times following administration; in combination with a biguanide antihyperglycemic agent, such as metformin, dosed twice daily; in combination with an omega-3 fatty acid derivative, such as icosapent ethyl, dosed twice daily; in combination with a flavonoid, such as fisetin, dosed daily; in combination with a T3 thyroid hormone, such as liothyronine, dosed either for two days in a row per week or dosed on separated days for no more than 3 days per week. In some preferred forms, the methods include administering a macrolide, such as rapamycin, dosed weekly to achieve blood levels below about 12 nanograms per ml of blood measured at about 60 hours plus or minus 3 hours following administration; in combination with a biguanide antihyperglycemic agent, such as metformin, dosed twice daily at about 500 mg to about 2000 mg; in combination with an omega-3 fatty acid derivative, such as icosapent ethyl, dosed twice daily at about 2.0 g to about 4.0 g; in combination with a flavonoid, such as fisetin, dosed daily at about 20.0 mg/kg patient body weight (which dose may be achieved by starting at a daily dose of about 200 mg and stepping up to the daily dose of about 20.0 mg/kg); in combination with a T3 thyroid hormone, such as liothyronine, dosed either for two days in a row per week or dosed on separated days for no more than 3 days per week at about 5.0 μg to about 10.0 μg. In some preferred forms, the methods include administering a composition that does not include a macrolide, such as rapamycin, when it is not clinically necessary.

In various embodiments, the methods may include administering the effective amount of the compositions to a patient through any suitable route of administration effective in delivering an amount of active agent or active agents to a patient. Suitable routes of administration include oral, intravascular, intramuscular, subcutaneous, parenteral, enteral, and rectal or the like.

In various embodiments, the methods may include administering the effective amount of the compositions comprised of each of the ingredients in a single administration form, such as a pill, tablet, capsule, oral solution, injection solution, infusion solution, or any of the forms described herein. In various embodiments, the methods may include administering the effective amount of the compositions from a kit comprising each of the individual ingredients, together with instructions for administering each ingredient. In some forms of the kit, certain ingredients will already be combined such that one, two, three, four, or more of the components or ingredients of the composition are in a single administration form as described herein.

EXAMPLE

Clinical Study of Metformin and Icosapent Ethyl

Fifty to 100 patients with biopsy-confirmed fatty liver disease with and without cirrhotic scarring are recruited for study. Fifty patients are further recruited for a control group. Liver enzymes are monitored among the patients. Half of the patients with biopsy confirmed fatty liver disease are administered a combination of metformin and icosapent ethyl. The remaining patients with biopsy-confirmed fatty liver disease are administered icosapent ethyl and metformin in combination with a vitamin supplement. All patients are administered a low fat diet.

Ultrasound testing is performed on all patients at initiation of the study and every 3 months thereafter for 1 year. At the end of 1 year, liver biopsy is performed on all patients to record histologic changes and liver enzyme levels.

This written description uses examples to disclose the subject matter herein, including the best mode, and also to enable any person skilled in the art to practice the subject matter disclosed herein, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of treating, reducing the incidence of, or reducing the severity of hepatic steatosis comprising administering an effective amount of a pharmaceutical composition of one or more mTOR inhibitors selected from the group consisting of an omega-3 fatty acid derivative, a biguanide antihyperglycemic agent, a flavonoid selected from the group consisting of fisetin and fisetin derivatives, a macrolide, and any combination thereof; and an effective amount of one or more thyroid hormones, wherein the one or more thyroid hormones include liothyronine.

2. The method of claim 1, wherein the omega-3 fatty acid derivative is icosapent ethyl.

3. The method of claim 1, wherein the biguanide antihyperglycemic agent is metformin.

4. The method of claim 1, wherein the flavonoid is selected from the group consisting of fisetin and a fisetin derivative.

5. The method of claim 1, wherein the macrolide is rapamycin.

6. The method of claim 1, wherein the pharmaceutical composition further comprises an effective amount of one or more other active agents selected from the group consisting of vitamin B derivatives, quercetin, resveratrol and NAD+.

* * * * *